United States Patent [19]

Cragoe, Jr. et al.

[11] 4,087,526
[45] May 2, 1978

[54] (3-AMINO-5-SUBSTITUTED-6-FLUOROPYRAZINOYL OR PYRAZAMIDO)-GUANIDINES AND THEIR DERIVATIVES BEARING SUBSTITUENTS ON THE GUANIDINO NITROGENS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 708,254

[22] Filed: Jul. 23, 1976

[51] Int. Cl.² .................. C07D 241/02; A61K 31/495
[52] U.S. Cl. .............................. 424/250; 424/248.54; 260/250 B; 544/107; 544/110; 544/120
[58] Field of Search ................. 260/250 BN, 247.2 A; 424/250, 248.54

[56] References Cited

U.S. PATENT DOCUMENTS

| 3,300,494 | 1/1967 | Cragoe | 260/250 BN |
| 3,313,813 | 4/1967 | Cragoe | 260/250 BN |

*Primary Examiner*—Donald G. Daus
*Assistant Examiner*—Jose Tovar
*Attorney, Agent, or Firm*—Michael C. Sudol, Jr.

[57] ABSTRACT

This invention is concerned with (3-amino-5-substituted-6-fluoropyrazinoyl or pyrazinamido)guanidine compounds and derivatives thereof bearing substituents on the guanidine nitrogens. These compounds possess useful natriuretic properties. Also included are processes for preparing these compounds and a novel intermediate used in the preparation of these compounds.

12 Claims, No Drawings

(3-AMINO-5-SUBSTITUTED-6-FLUOROPYRAZINOYL OR PYRAZAMIDO)-GUANIDINES AND THEIR DERIVATIVES BEARING SUBSTITUENTS ON THE GUANIDINO NITROGENS

BACKGROUND OF THE INVENTION

Similar type compounds, particularly (3-amino-5-substituted-6-halopyrazinoyl)guanidines and (3-amino-5-substituted-6-halopyrazinamido)guanidines have been disclosed in U.S. Pat. Nos. 3,313,813 and 3,300,494, respectively. However, in neither patent is applicants' (3-amino-5-substituted-6-fluoropyrazinoyl)guanidine or pyrazinamido-guanidines disclosed.

In U.S. Pat. No. 3,313,813 the 6-fluoro derivative has not been claimed or disclosed because the 6-position was described in col. 1 lines 28–30 of said patent as halogen or halogen-like radicals, such as chloro, bromo, iodo or trifluoromethyl.....

Similarly in U.S. Pat. No. 3,300,494, although the 6-halo derivative was claimed in the specification in col. 1, lines 20–22, the 6-substituent is described as a halogen substituent such as chlorine, bromine, iodine, or a trihalomethyl radical.... Nowhere in these patents is a 6-fluoro derivative specifically disclosed or claimed. In fact, none could be specifically disclosed as at that time, the immediate precursor needed for preparing applicants' compounds, namely the lower alkyl-3-amino-5-substituted-6-fluoro pyrazinoates was unknown. At the time of filing the two U.S. patents mentioned above, a method for introduction of a 6-fluoro group onto the pyrazinoate was not known.

A unique and unexpected advantage of the (3-amino-5-substituted-6-fluoropyrazinoyl or pyrazinamido)-guanidines of this invention in comparison to other 6-halo analogs is their markedly lower toxicities. For example, the acute oral toxicity of (3,5-diamino-6-chloropyrazinoyl)guanidine in mice is over ten times as toxic as the corresponding 6-fluoro analog.

DESCRIPTION OF INVENTION

This application relates to (3-amino-5-substituted-6-fluoropyrazinoyl or pyrazinamido)guanidine compounds which can be represented by the following structure:

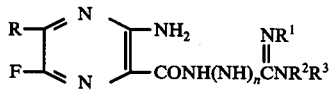

wherein
R is amino, lower alkylamino wherein the alkyl groups have up to 5 carbon atoms, or diloweralkylamino wherein the alkyl groups have up to 5 carbon atoms;
$R^1$ is hydrogen or lower alkyl having up to 5 carbon atoms;
$R^2$ is hydrogen, lower alkyl having up to 5 carbon atoms, lower alkenyl having up to 3 carbon atoms, hydroxyloweralkyl, aryl such as phenyl or substituted aryl wherein the substituent is halo or lower alkyl having up to 3 carbon atoms, aralkyl preferably benzyl or phenethyl or substituted aralkyl wherein the substituents are halo or lower alkyl having up to 3 carbon atoms;
$R^1$ and $R^2$ can be joined to form an alkylene bridge of from 2 to 3 carbon atoms, thus forming a carbon bridged chain;
$R^3$ is hydrogen or lower alkyl having up to 5 carbon atoms;
$R^2$ and $R^3$ can be joined to form a heterocyclic ring having from 3 to 6 carbon atoms with the nitrogen atom to which they are attached;
$R^2$ and $R^3$ can also be joined to form a heterocyclic ring with the nitrogen atom to which they are attached, said heterocyclic ring having additional oxygen or nitrogen atoms in addition to the nitrogen atom to which $R^2$ and $R^3$ are attached such as to form a piperidine or a morpholine ring;
$n$ is 0 or 1;
and the non-toxic pharmaceutically acceptable salts thereof.

A preferred aspect of this invention are those compounds of Formula I above wherein
R is amino;
$R^1$, $R^2$ and $R^3$ are hydrogen;
$n$ is 0 or 1; and
the non-toxic, pharmaceutically acceptable salts thereof.

As described above included in the invention are the non-toxic pharmaceutically acceptable salts preferably the non-toxic pharmaceutically acceptable acid addition salts derived from a non-toxic pharmaceutically acceptable acid such as hydrochloric acid, hydrobromic acid, hydriodic acid, sulfuric acid, methanesulfonic acid, isethionic acid and the like.

Specific preferred compounds of this invention can be such as (3,5-diamino-6-fluoropyrazinoyl)guanidine and the hydrochloride salt thereof and (3,5-diamino-6-fluoropyrazinamido)guanidine and the hydrochloride salt thereof.

The compounds of this invention are useful because they possess diuretic and natriuretic properties. They differ from most of the known, effective diuretic agents, however, in that the compounds of this invention selectively enhance the excretion of sodium ions without causing an increase in excretion of potassium ions. The potassium loss, which is caused by known diuretics, often results in a severe muscular weakness. Since the compounds of this invention are essentially free of this potassium depletion, they have this decided advantage as diuretics. As diuretic agents, they can be used for the treatment of edema, hypertension and other diseases known to be responsive to this therapy.

It has also been found as another feature of this invention that when co-administered with other diuretic agents known to enhance the elimination of potassium ions along with sodium ions, the novel pyrazinoylguanidines of this invention will reduce the excretion of potassium ions and thus overcome this undesirable property of other diuretic agents. The compounds of this invention, therefore, are useful in combination with other classes of diuretic agents such as hydrochlorothiazide to prevent the loss of potassium which the other diuretics otherwise would cause to be eliminated. In addition, the compounds of this invention are useful by themselves as diuretic and/or saluretic agents.

The products of this invention can be administered to man or animals in the form of pills, tablets, capsules, elixirs, injectable preparations and the like and can comprise one or more of the compounds of this invention as the only essential active ingredient of the pharmaceutical formulation or, as mentioned above, the novel compound(s) can be combined in pharmaceutical formulations with other diuretic agents or, indeed, other therapeutic agents.

The compounds of this invention are advantageously administered at a dosage range of from about 5 mg./day to about 750 mg./day or at a somewhat higher or lower dosage at the physician's discretion, preferably in subdivided amounts on a 2 to 4 times a day regimen.

The compounds of this invention can be made by the process shown in the following equation:

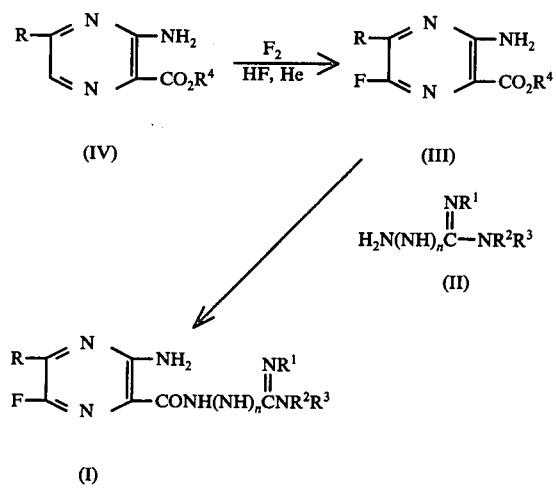

wherein R, $R^1$, $R^2$, $R^3$ and $n$ are as previously defined and $R^4$ is lower alkyl or benzyl.

The above described synthesis involves the reaction of a lower alkyl 3-amino-5-substituted pyrazinoate (Compound I) with fluorine gas diluted with helium in a liquid hydrogen fluoride solvent to prepare the lower alkyl 3-amino-5-substituted-6-fluoropyrazinoate (Compound III) and a further reaction of Compound III with guanidine or aminoguanidine or derivatives of Compound II to form the desired product of Compound I.

The first step of this synthesis involves the reaction of a lower alkyl 3-amino-5-substituted-pyrazinoate with fluorine gas diluted with helium-liquid hydrogen fluoride to form the 6-fluoro derivatives (Compound III). Although lower alkyl esters are named with preference being for the methyl ester, the ester can be that of any other alcohol as it will be noted that this ester radical does not appear in the desired end product.

In this particular reaction, the fluorine gas which is diluted with helium is bubbled through hydrogen fluoride, the starting material Formula IV being already dissolved in the liquid hydrogen fluoride. The reaction is carried out at very low temperatures preferably at about −78° C. The reaction is generally complete in 2 to 8 hours. The intermediate product III which itself is a novel compound can be isolated by evaporation of the liquid hydrogen fluoride after which the intermediate Formula III can be purified by sublimation or recrystallization from the appropriate solvent.

In the second step of the process, namely the reaction of the 6-fluoro ester (Formula III) with guanidine or aminoguanidine or derivatives thereof (Formula II) to form the desired products (Formula I) is preferably carried out under anhydrous conditions either with or without a solvent such as methanol, ethanol, isopropyl alcohol or other solvents. The reaction may be carried out at room temperature or by heating on a steam bath for 1 minute to 2 hours or longer. The desired product usually is recovered from the cooled reaction mixture by trituration with water. Purification frequently is carried out by converting the product to a salt which can be recrystallized or the base can be regenerated by addition of aqueous alkali.

The following examples are illustrative of the methods by which the products of this invention can be prepared and are not to be considered as limiting the invention to the particular procedural conditions employed or to the particular compounds prepared thereby.

EXAMPLE 1

(3,5-Diamino-6-fluoropyrazinoyl)guanidine

Step A: Methyl 3,5-diamino-2-pyrazinoate

A mixture of methyl 3,5-diamino-6-chloropyrazinoate (14.2 g., 0.07 mole) 5% Pd-C catalyst (9 g.) magnesium oxide (4.0 g., 0.1 mole) and methanol (250 ml.) is shaken in an atmosphere of hydrogen for 18 hours at 25° C. at an initial pressure of 2.1 kg./cm². The reaction mixture is filtered and the solids extracted with a hot solution of 2-propanol (500 ml.) and water (250 ml.). The methanol and 2-propanol-water extract are combined and concentrated to a volume of 100 ml. to give 10 g. (85%) of methyl 3,5-diaminopyrazinoate which melts at 252°–4° C.

Elemental analysis $C_6H_8N_4O_2$ Calc.: C, 42.85; H, 4.80; N, 33.32; Found: C, 43.15; H, 4.76; N, 33.11.

Step B: Methyl 3,5-diamino-6-fluoropyrazinoate

In a Kel-F$^R$ reactor cooled to −78° C in an acetone-dry ice bath is placed methyl 3,5-diaminopyrazinoate (6g.) and liquid hydrogen fluoride (70 ml.). A stream of fluorine-helium mixture (1:4 v/v) is passed through the solution for 5½ hours at −78° C. followed by a vigorous stream of nitrogen to remove the solvent. The reaction residue is treated with conc. hydrochloric acid (60 ml.), evaporated to dryness, dissolved in water (75 ml.) and neutralized with aqueous sodium hydroxide to give methyl 3,5-diamino-6-fluoropyrazinoate (5 g.) which is purified by sublimation (140°–50° C., 0.05 mm Hg.) and recrystallization from 2-propanol.

Elemental analysis $C_6H_7FN_4O_2$ Calc.: C, 38.71: H, 3.79; N, 30.10; F, 10.21; Found: C, 38.49; H, 3.58; N, 29.96; F, 10.45.

Step C: (3,5-Diamino-6-fluoropyrazinoyl)guanidine

To a stirred solution of sodium methoxide (1.45 g.) in methanol (25 ml.) is added guanidine hydrochloride (3.0 g.). After ¼ hour, the sodium chloride which separates is filtered, the guanidine solution distilled to 6 ml., treated with the methyl (3,5-diamino-6-fluoropyrazinoate (960 mg.) and heated on a steam bath for 5 minutes. Trituration of the reaction with water provides (3,5-diamino-6-fluoropyrazinoyl)guanidine (600 mg.) which melts at 233° C. after reprecipitation from aqueous hydrochloric acid with aqueous sodium hydroxide.

Elemental analysis $C_6H_8FN_7O$ Calc.: C, 33.80; H, 3.78; F, 8.91; Found: C, 33.97; H, 3.91; F, 9.18.

Dissolving the (3,5-diamino-6-fluoropyrazinoyl)-guanidine in hot aqueous hydrochloric acid, hydrobromic acid, hydriodic acid, sulfuric acid, methanesulfonic acid or isethionic acid affords the corresponding hydrochloride, hydrobromide, hydroiodide, sulfate, methosulfonate or isethionate salt of (3,5-diamino-6-fluoropyrazinoyl)guanidine.

EXAMPLE 2

Step A

Following the procedure of Example 1, Step A, but substituting the following major reactant in place of methyl 3,5-diamino-6-chloropyrazinoate reactant in Example 1, Step A there is obtained the appropriately listed product.

| Reactant | Product |
|---|---|
| methyl 3-amino-5-dimethylamino-6-chloropyrazinoate | methyl 3-amino-5-dimethylaminopyrazinoate |
| methyl 3-amino-5-methylamino-6-chloropyrazinoate | methyl 3-amino-5-methylaminopyrazinoate |
| methyl 3-amino-5-ethylamino-6-chloropyrazinoate | methyl 3-amino-5-ethylaminopyrazinoate |
| methyl 3-amino-5-propylamino-6-chloropyrazinoate | methyl 3-amino-5-propylaminopyrazinoate |
| methyl 3-amino-5-isopropylamino-6-chloropyrazinoate | methyl 3-amino-5-isopropylaminopyrazinoate |
| methyl 3-amino-5-diethylamino-6-chloropyrazinoate | methyl 3-amino-5-diethylaminopyrazinoate |

Step B

Following the procedure of Example 1, Step B, but substituting the following major reactant in place of the methyl 3,5-diamino-2-pyrazinoate reactant in Example 1, Step B, there is obtained the appropriately listed end product.

| Reactant | Product |
|---|---|
| methyl 3-amino-5-dimethylaminopyrazinoate | methyl 3-amino-5-dimethylamino-6-fluoropyrazinoate |
| methyl 3-amino-5-methylaminopyrazinoate | methyl 3-amino-5-methylamino-6-fluoropyrazinoate |
| methyl 3-amino-5-ethylaminopyrazinoate | methyl 3-amino-5-ethylamino-6-fluoropyrazinoate |
| methyl 3-amino-5-propylaminopyrazinoate | methyl 3-amino-5-propylamino-6-fluoropyrazinoate |
| methyl 3-amino-5-isopropylaminopyrazinoate | methyl 3-amino-5-isopropylamino-6-fluoropyrazinoate |
| methyl 3-amino-5-diethylaminopyrazinoate | methyl 3-amino-5-diethylamino-6-fluoropyrazinoate |

Step C

Following the procedure of Example 1, Step C, but substituting the following major reactant in place of the methyl 3,5-diamino-6-fluoropyrazinoate reactant in Example 1, Step C, there is obtained the appropriately listed end product.

| Reactant | Product |
|---|---|
| methyl 3-amino-5-dimethylamino-6-fluoropyrazinoate | (3-amino-5-dimethylamino-6-fluoropyrazinoyl)-guanidine |
| methyl 3-amino-5-methylamino-6-fluoropyrazinoate | (3-amino-5-methylamino-6-fluoropyrazinoyl)-guanidine |
| methyl 3-amino-5-ethylamino-6-fluoropyrazinoate | (3-amino-5-ethylamino-6-fluoropyrazinoyl)-guanidine |
| methyl 3-amino-5-propylamino-6-fluoropyrazinoate | (3-amino-5-propylamino-6-fluoropyrazinoyl)guanidine |
| methyl 3-amino-5-isopropylamino-6-fluoropyrazinoate | (3-amino-5-isopropylamino-6-fluoropyrazinoyl)-guanidine |
| methyl 3-amino-5-diethylamino-6-fluoropyrazinoate | (3-amino-5-diethylamino-6-fluoropyrazinoyl)-guanidine |

EXAMPLES 3 – 15

Following the procedure of Example 1, Step C, but substituting the following major reactant in place of the guanidine reactant in Example 1, Step C, there is obtained the appropriately listed end product.

| Ex. | Reactant | Product |
|---|---|---|
| 3 | (2-hydroxyethyl)guanidine | 1-(3,5-diamino-6-fluoro-pyrazinoyl)-3-(2-hydroxyethyl)guanidine |
| 4 | methylguanidine | (1-(3,5-diamino-6-fluoro-pyrazinoyl)-3-methyl-guanidine |
| 5 | phenylguanidine | (1-(3,5-diamono-6-fluoro-pyrazinoyl)-3-phenyl-guanidine |
| 6 | benzylguanidine | (1-(3,5-diamino-6-fluoro-pyrazinoyl)-3-benzyl-guanidine |
| 7 | 1,1-dimethylguanidine | (1-(3,5-diamino-6-fluoro-pyrazinoyl)-3,3-dimethyl-guanidine |
| 8 | 1,2-dimethylguanidine | (1-(3,5-diamino-6-fluoro-pyrazinoyl)-2,3-dimethyl-guanidine |
| 9 | 1,1-dibutylguanidine | (1-(3,5-diamino-6-fluoro-pyrazinoyl)-3,3-dibutyl-guanidine |
| 10 | 1,1-diethylguanidine | |
| 11 | 1-amidinopyrrolidine | (1-(3,5-diamino-6-fluoro-pyrazinoyl)-3,3-tetra-methyleneguanidine |
| 12 | 4-amidinomorpholine | (1-(3,5-diamino-6-fluoro-pyrazinoyl)-3,3-(3-oxa-pentamethylene)guanidine |
| 13 | allylguanidine | (1-(3,5-diamino-6-fluoro-pyrazinoyl)-3-allyl-guanidine |
| 14 | aminoguanidine | (3,5-diamino-6-fluoropyrazinamido)guanidine |
| 15 | 2-amino-2-imidazoline | 2-(3,5-diamino-6-fluoropyrazinamido)-2-imidazoline |
| 16 | 1-amino-3-(2-hydroxyethyl)guanidine | 1-(3,5-diamino-6-fluoropyrazinamido)-3-(2-hydroxyethyl(guanidine |

EXAMPLE 7

| Dry filled capsule containing 25 mg. of active ingredient | Per capsule |
|---|---|
| (3,5-diamino-6-fluropyrazinoyl)-guanidine hydrochloride | 25 mg. |
| lactose | 298 mg. |
| magnesium stearate | 2 mg. |
| Mixed powders | 325 mg |

Mix the (3,5-diamino-6-fluoropyrazinoyl)guanidine hydrochloride from Example 1, lactose and magnesium stearate and reduce to a No. 60 mesh powder.

The above formulations can be employed to prepare compressed tablets or capsules of other novel compounds of this invention hereinbefore described.

Following the above procedure a dry filled capsule containing 25 mg. of (3,5-diamino-6-fluoropyrazinamido)guanidine can be prepared by using 25 mg. of this latter compound in place of 25 mg. of the (3,5-diamino-6-fluoropyrazinoyl)guanidine hydrochloride used above.

What is claimed is:
1. A compound of the formula:

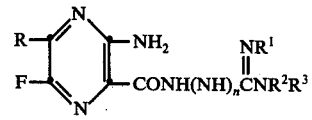

wherein
R is amino, lower alkylamino having up to 5 carbon atoms, or diloweralkylamino having up to 5 carbon atoms;

$R^1$ is hydrogen or lower alkyl having up to 5 carbon atoms;

$R^2$ is hydrogen, lower alkyl having up to 5 carbon atoms, hydroxy ethyl, lower alkenyl having up to 3 carbon atoms, phenyl, benzyl or phenethyl, halo or lower alkyl substituted phenyl or halo or lower alkyl substituted benzyl or phenethyl;

$R^1$ and $R^2$ are joined to form an alkylene bridge of 2 carbon atoms;

$R^3$ is hydrogen or lower alkyl having up to 5 carbon atoms;

$R^2$ and $R^3$ are joined to form a pyrrolidine or morpholine ring with the nitrogen atom to which they are attached;

$n$ is 0;

and the non-toxic pharmaceutically acceptable salts thereof.

2. A compound of the formula:

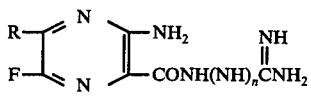

wherein R is amino, lower alkylamino wherein the alkyl can have from 1 to 5 carbon atoms, or diloweralkylamino wherein the alkyl group can have from 1 to 5 carbon atoms; $n$ is 0 and the pharmaceutically acceptable non-toxic salts thereof.

3. A compound of claim 2 wherein R is amino, and $n$ is 0 thus forming (3,5-diamino-6-fluoropyrazinoyl)guanidine and the pharmaceutically acceptable non-toxic salts.

4. A compound of claim 3 wherein the salt is the hydrochloride, thus forming (3,5-diamino-6-fluoropyrazinoyl)guanidine hydrochloride.

5. A compound of claim 2 wherein R is dimethylamino, and $n$ is 0, thus forming (3-amino-5-dimethylamino-6-fluoropyrazinoyl)guanidine and the pharmaceutically acceptable non-toxic salts.

6. A compound of claim 2 wherein R is isopropylamino, and $n$ is 0, thus forming (3-amino-5-isopropylamino-6-fluoropyrazinoyl)guanidine and the pharmaceutically acceptable non-toxic salts.

7. A pharmaceutical composition consisting essentially of a compound of the formula:

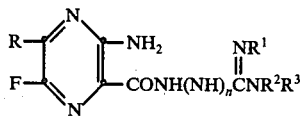

wherein

R is amino, lower alkylamino having up to 5 carbon atoms, or diloweralkylamino having up to 5 carbon atoms;

$R^1$ is hydrogen or lower alkyl having up to 5 carbon atoms;

$R^2$ is hydrogen, lower alkyl having up to 5 carbon atoms, hydroxy ethyl, lower alkenyl having up to 3 carbon atoms, phenyl, benzyl or phenethyl, halo or lower alkyl substituted phenyl or halo or lower alkyl substituted benzyl or phenethyl;

$R^1$ and $R^2$ are joined to form an alkylene bridge of 2 carbon atoms;

$R^3$ is hydrogen or lower alkyl having up to 5 carbon atoms;

$R^2$ and $R^3$ are joined to form a pyrrolidine or morpholine ring with the nitrogen atom to which they are attached;

$n$ is 0;

and the non-toxic pharmaceutically acceptable salts thereof.

8. A pharmaceutical composition consisting essentially of a compound of the formula:

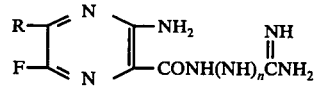

wherein R is amino, loweralkylamino or diloweralkylamino wherein the alkyl group can have from 1 to 5 carbon atoms; $n$ is 0 and the pharmaceutically acceptable non-toxic salts thereof and an inert pharmaceutical carrier.

9. A pharmaceutical composition according to claim 8 wherein the compound is (3,5-diamino-6-fluoropyrazinoyl)guanidine or a non-toxic pharmaceutically acceptable salt thereof.

10. A method of treating edema and/or hypertension which consists essentially of administering to a patient in need of such treatment a compound of the formula:

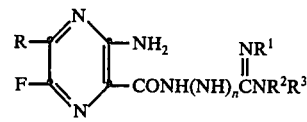

wherein

R is amino, lower alkylamino having up to 5 carbon atoms, or diloweralkylamino having up to 5 carbon atoms;

$R^1$ is hydrogen or lower alkyl having up to 5 carbon atoms;

$R^2$ is hydrogen, lower alkyl having up to 5 carbon atoms, hydroxy ethyl, lower alkenyl having up to 3 carbon atoms, phenyl, benzyl or phenethyl, halo or lower alkyl substituted phenyl or halo or lower alkyl substituted benzyl or phenethyl;

$R^1$ and $R^2$ are joined to form an alkylene bridge of 2 carbon atoms;

$R^3$ is hydrogen or lower alkyl having up to 5 carbon atoms;

$R^2$ and $R^3$ are joined to form a pyrrolidine or morpholine ring with the nitrogen atom to which they are attached;

$n$ is 0;

and the non-toxic pharmaceutically acceptable salts thereof.

11. A method of treating edema and/or hypertension which consists essentially of administering to a patient in need of such treatment 5 mg./day to about 750 mg./day of a compound of the formula:

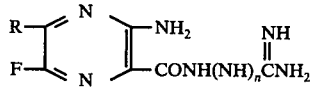

wherein R is amino, lower alkylamino or diloweralkylamino wherein the alkyl group can have from 1 to 5 carbon atoms; $n$ is 0 and the pharmaceutically acceptable non-toxic salts thereof.

12. A method of treatment according to claim 11 wherein the compound to be administered is (3,5-diamino-6-fluoropyrazinoyl)guanidine or a non-toxic pharmaceutically acceptable salt thereof.

* * * * *